(12) United States Patent
Zweymüller

(10) Patent No.: US 6,613,094 B2
(45) Date of Patent: *Sep. 2, 2003

(54) SHAFT FOR ANCHORING A HIP JOINT PROSTHESIS IN THE FEMUR

(75) Inventor: Karl Zweymüller, Vienna (AT)

(73) Assignee: Plus Endoprothetik (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/548,576

(22) Filed: Apr. 13, 2000

(65) Prior Publication Data

US 2002/0183854 A1 Dec. 5, 2002

(30) Foreign Application Priority Data

Apr. 13, 1999 (DE) .......................... 199 16 630

(51) Int. Cl.$^7$ ................................................ A61F 2/36
(52) U.S. Cl. .................................................. 623/23.35
(58) Field of Search ........................ 623/23.35, 22.43, 623/22.46, 23.11, 23.14, 23.24, 23.26, 23.28, 23.29

(56) References Cited

U.S. PATENT DOCUMENTS

| 4,404,693 A | 9/1983 | Zweymüller |
| 4,664,668 A | 5/1987 | Beck et al. |
| 4,728,334 A | 3/1988 | Spotorno |
| 4,813,962 A | 3/1989 | Deckner et al. |
| 4,908,035 A | 3/1990 | Deckner et al. |
| 4,979,958 A | * 12/1990 | Niwa et al. ................... 623/23 |
| 5,133,770 A | 7/1992 | Zweymüller et al. |
| 5,456,717 A | * 10/1995 | Zweymuller et al. ......... 623/16 |
| 6,224,634 B1 | 5/2001 | Keller |

FOREIGN PATENT DOCUMENTS

| GB | 1409054 | * 10/1975 | .................. 623/23 |

* cited by examiner

*Primary Examiner*—Bruce Snow
(74) *Attorney, Agent, or Firm*—Knobbe, Martens, Olson & Bear, LLP

(57) ABSTRACT

A profiled shaft for anchoring a hip-joint prosthesis in the femur is disclosed, with a shaft section and a fixation section that is formed at the end of the shaft section and that serves for the fixation of a spherical joint head, wherein the shaft section on the lateral surface in the proximal region merges with a trochanter wing at the edges of which beveled surfaces are formed. The essential point of the invention is that the angle formed between the plane of a beveled surface and the plane of the adjacent lateral surface is smaller than 135° and larger than 90°. In a construction of this kind the advantage of an improved filling of the empty space in the trochanter-wing region is achieved.

2 Claims, 5 Drawing Sheets

PROXIMAL

SHAFT FOR ANCHORING A HIP JOINT PROSTHESIS IN THE FEMUR

The invention relates to a profiled shaft for anchoring a hip-joint prosthesis in the femur, with a shaft section and a fixation section, formed at the end of the shaft section, which serves for the fixation of a spherical joint head, wherein the medial narrow side of the shaft section merges with a continuously curved arch that ends in the region of the fixation section, and wherein the lateral side of the shaft section in its proximal region merges with a trochanter wing on which the corners are beveled to form slanted surfaces (facets).

A profiled shaft of this kind for anchoring a hip-joint prosthesis in the femur is known, for example, from U.S. Pat. No. 5,456,717.

The purpose of the beveled surfaces (facets) is to achieve a better fit of the trochanter-wing region of the profile shaft when it is seated in the femoral opening.

The conventional practice is to use a facet angle of 45° or 135° (angle between the plane of the lateral side and the plane of the adjacent facet of interest).

However, this specification of the facet angle has proved to produce comparatively large empty spaces in the corner regions of the trochanter wing.

The object of the present invention is to create a profiled shaft of the above-mentioned kind, for the anchoring section of a hip-joint prosthesis in the femur, such that the empty space in the trochanter-wing region can be substantially reduced by particularly simple measures.

This object is achieved in accordance with the invention by developing the profiled shaft of the kind cited above in such a way that the angle between the plane of a beveled surface (facet) and the plane of the adjacent lateral side surface is made smaller than 135° and larger than 90°.

An especially advantageous and effective embodiment of the invention further consists in restricting the above-mentioned angle to the range between 100° and 120°.

Furthermore, an especially improved filling of the empty space in the trochanter-wing region can be achieved by forming a beveled surface (facet) at the transition between the lateral surface of the shaft and the anterior (broad) surface, and between the lateral surface of the shaft and the posterior (broad) surface of the shaft.

The invention is further characterized in that the beveled surfaces are constructed as facets with unequal angles at their two ends.

An especially advantageous embodiment of the invention, in the case of a profiled shaft in which the shaft section on its lateral aspect merges with the trochanter wing in the form of a continuously bending curve, consists in a change in the configuration of each of the beveled surfaces in the region of the continuously bending curve, such that in the direction from the shaft region to the trochanter region an equal-angled facet changes to one with unequal angles.

In this case the change from equal-angled facet to unequal-angled facet can take the form of a gradual transition or, in an alternative embodiment, there can be a stepwise change from equal-angled facet to unequal-angled facet.

In the following the invention is explained in detail with reference to exemplary embodiments and the drawings, wherein FIG. 1 is a perspective view of a profiled shaft for anchoring a hip-joint prosthesis in the femur with characteristics according to the invention;

Figure 1:
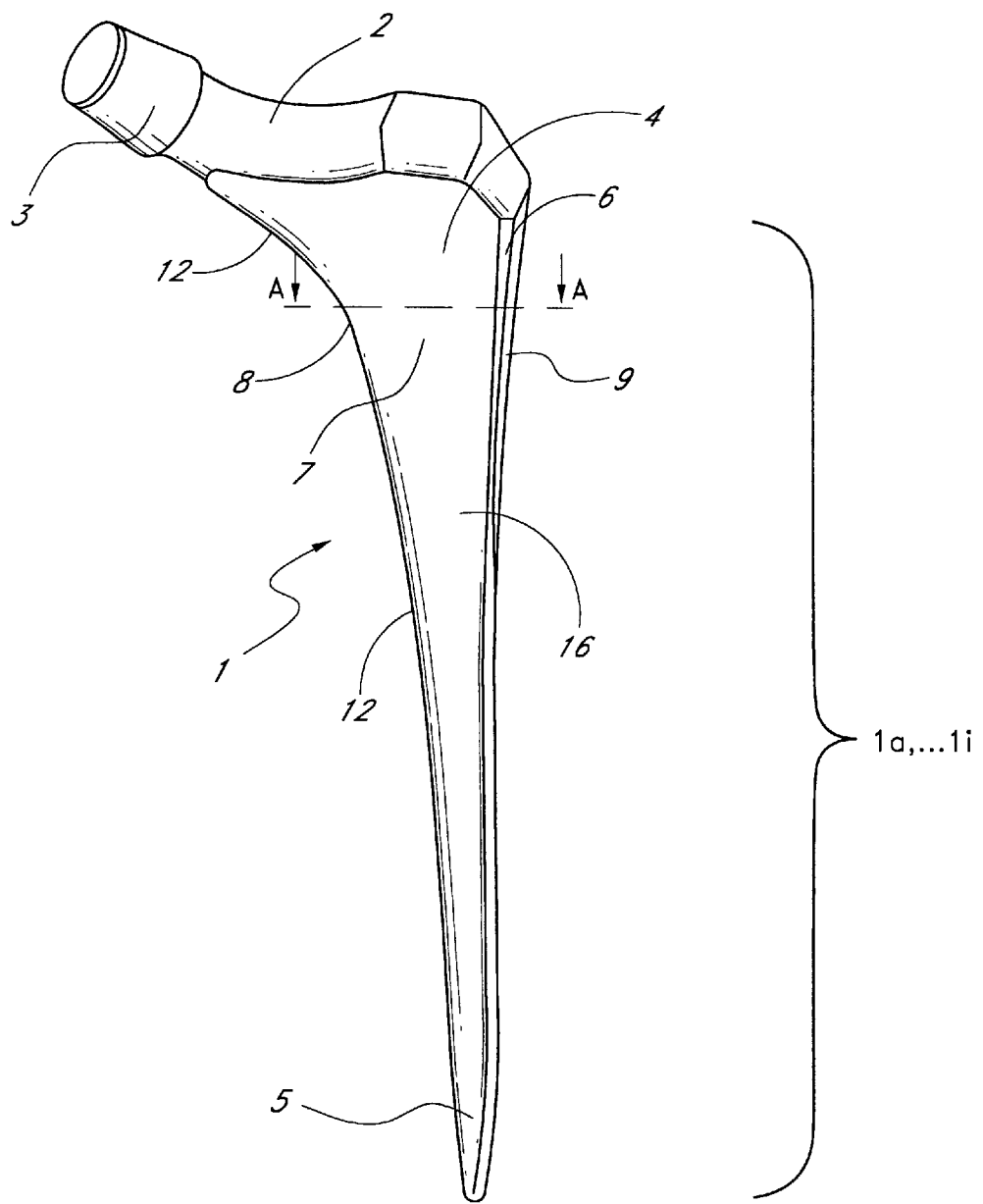

FIG. 1 gives a perspective view of an exemplary embodiment of a profiled shaft in which the characteristics according to the present invention are implemented. The profiled shaft shown here is in general designated by 1 and comprises a lower, distal, narrow end 5 and a section 7 that expands upward and in its upper end region is continuous with a section 3 in the shape of a truncated cone that serves for the fixation of a spherical joint head. On the medial narrow side 12 in the proximal region the shaft has the form of a continuously bending curve 8, which ultimately ends in the region of the fixation section 2.

On the lateral side (anterior broad side 16) the shaft section merges in its proximal region with a trochanter wing 4, on which beveled corner surfaces 6 (facets) are formed. The anterior broad side 16 is substantially parallel to a posterior broad side 20 (FIG. 2).

In the conventional construction the angle between the plane of each beveled surface 6 and that of the adjacent lateral surface 9 is 135° (or 45°).

Figure 2:
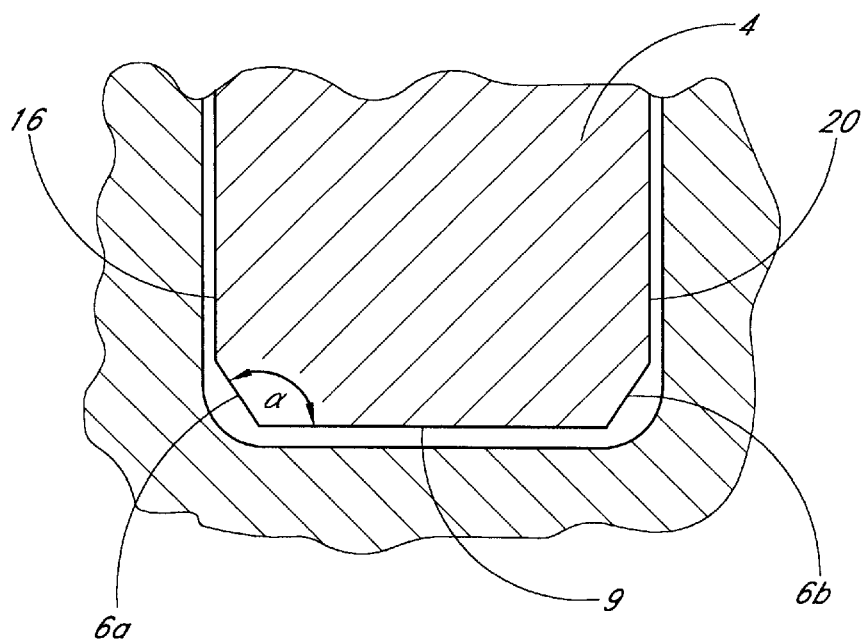
FIG. 2 is a sectional, partially exploded drawing of a profiled shaft in the implanted state with characteristics according to the invention.

As can be seen in FIG. 2, which shows a partial view of a section along the line A—A in FIG. 1 (in implanted state), the beveled surfaces 6a and 6b are oriented with respect to the plane of the lateral surface 9 at a steeper angle in comparison with the state of the art; that is, the angle α formed between the plane of a beveled surface 6a or 6b and the plane of the lateral surface 9 adjacent to the respective beveled surface is smaller than 135° and larger than 90°.

In a particularly preferred embodiment of the invention the angle α is within the range between 100° and 120°.

Figure 3:
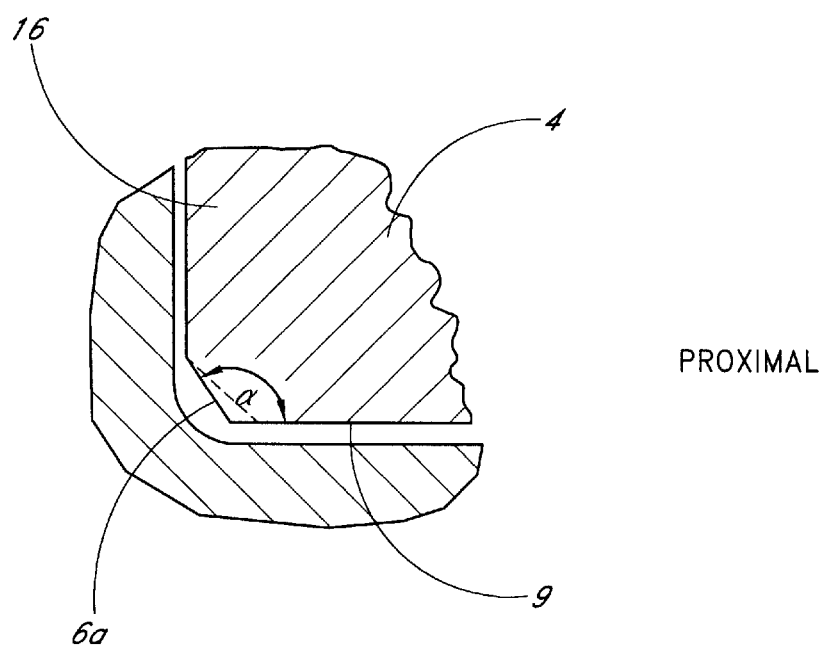
FIG. 3 is an enlarged view of a corner region of the trochanter wing in the implanted state.

In FIG. 3 the left corner region is shown, again in section, as an enlarged partial view in which the embodiment according to the state of the art is indicated by a dashed line. It is evident in FIG. 3 that in the construction in accordance with the invention the empty space between the trochanter-wing region and the surrounding bone is very much smaller than, for comparison, in the conventional construction; that is, the construction in accordance with the invention achieves a better filling of the empty space in the trochanter-wing region.

It should be noted that in the construction in accordance with the invention a beveled surface (facet) is formed at the transition between the lateral surface of the shaft and trochanter wing and the anterior surface as well as at the transition between the lateral surface of the shaft and trochanter wing and the posterior surface of the shaft.

The beveled surfaces in the construction in accordance with the invention are in particular formed as facets with unequal angles at their two ends.

Figure 4:
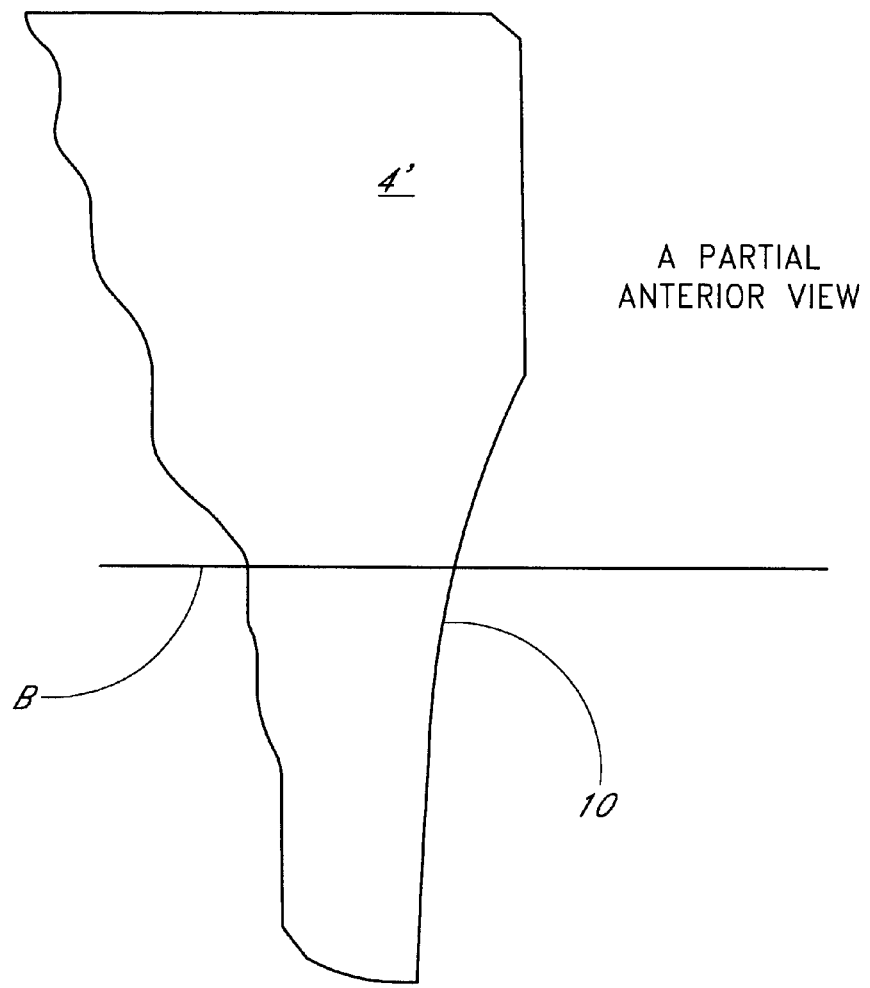
FIG. 4 is a partial anterior view of the upper section of the profiled shaft with characteristics according to the invention.

Another embodiment of the present invention is shown schematically in FIG. 4. Here the upper section of the profile shaft, with the trochanter wing 4', is shown enlarged. In the embodiment shown in FIG. 4 the transition between lateral surface of the shaft section in its proximal region and the trochanter wing 4' has the form of a continuously bending curve 10.

Figure 5:
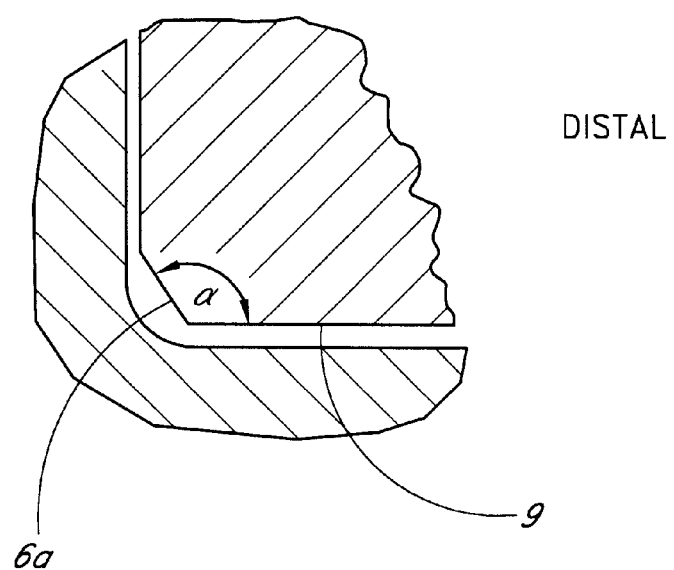
FIG. 5 is an enlarged view of a corner region of the shaft at a distal portion.
Figure 6:
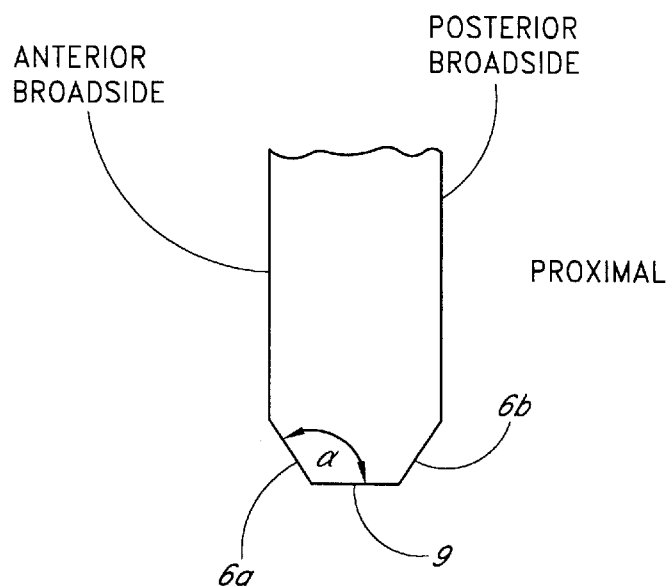
FIG. 6 is a cross section of a profiled shaft with unequal angles between a beveled surface and a plane of an adjacent lateral surface.
Figure 7:
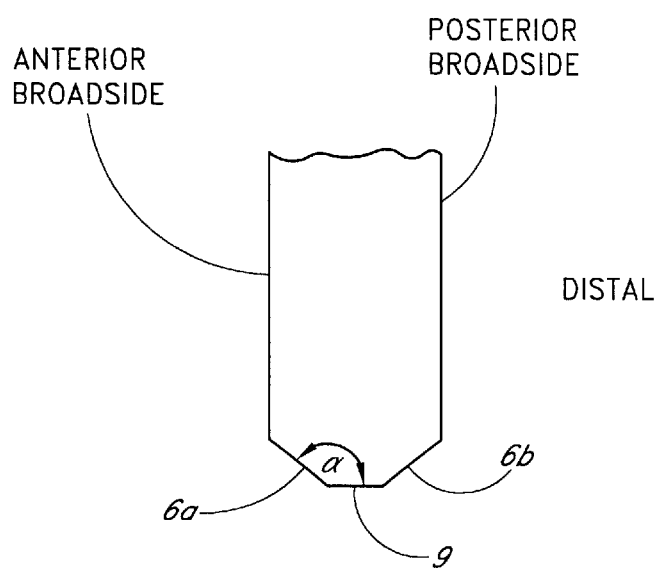
FIG. 7 is a cross section of a profiled shaft with equal angles between a beveled surface and a plane of an adjacent lateral surface.

The essential feature of this embodiment is that within the region of the continuously bending curve 10, at about the level of reference line B, each of the beveled corner surfaces varies in its orientation along the direction from the shaft region to the trochanter region, changing from an equal-angled facet as shown in FIGS. 5 and 7 to a facet with unequal angles as shown in FIG. 6.

This embodiment offers the special advantage that the facet with unequal angles is mechanically simpler to produce, for example by rotating the shaft about its long axis during manufacture or by a corresponding rotation of the machining tool.

In an advantageous configuration of the embodiment shown in FIG. 4 the change from equal-angled facet to facet with unequal angles takes the form of a smooth transition.

Another embodiment consists in changing from equal-angled facet to facet with unequal angles in a stepwise manner.

It should be pointed out that the present invention is not limited to the exemplary embodiments shown here, and that a number of modifications and changes can be undertaken without exceeding the scope of the present invention.

For example, it would be possible to construct not only one transitional region from equal-angled facet to facet with unequal angles, as described above, but rather to incorporate several transitions of this kind within the region of continuous curvature.

LIST OF REFERENCE NUMERALS

| | |
|---|---|
| 1= | Profiled shaft |
| 2= | Fixation section |
| 3= | Section in form of truncated cone |
| 4= | Trochanter-wing region |
| 5= | Distal end |
| 6= | Beveled edge surface |
| 6a, 6b= | Beveled edge surface |
| 7= | Expanding section |
| 8= | Continuously curving arch |
| 9= | Lateral surface |
| 10= | Continuously curving arch |
| A—A= | Line |
| 4'= | Trochanter wing |
| α= | Angle |

What is claimed is:

1. A profiled shaft for anchoring a hip-joint prosthesis in a femur, comprising:

a shaft section having a generally rectangular cross section and having a proximal region, a distal region, a lateral side and a medial narrow side, wherein a trochanter wing is continuous with the lateral side of the shaft section in the proximal region, wherein the trochanter wing has an anterior broad side and a posterior broad side that are substantially perpendicular to the lateral side, wherein the trochanter wing has beveled edge surfaces, and wherein an angle formed between a plane of a beveled surface and a plane of an adjacent lateral surface is smaller than 135° and larger than 120°, wherein the shaft section on the lateral side merges with the trochanter wing in the form of a continuously bending curve, wherein each beveled edge surface has a first end at the lateral surface and a second end at the broad side, wherein the angle at the first end is different from another angle at the second end within the shaft section, wherein the angle at the first end is equal to the another angle at the second end at the trochanter wing, and wherein each beveled edge surface changes from an equal-angled facet to a facet with unequal angles within the region of the continuous curvature and in a direction from the shaft section to the trochanter region; and a fixation section formed at an end of the shaft section, which serves for a fixation of a spherical joint head, wherein the medial narrow side of the shaft section in the proximal region merges with a continuously curved arch that ends in a region of the fixation section.

2. The profiled shaft according to claim 1, wherein the change from equal-angled facet to facet with unequal angles takes the form of a smooth transition.

* * * * *